United States Patent
Koseoglu et al.

(10) Patent No.: US 11,548,842 B1
(45) Date of Patent: Jan. 10, 2023

(54) CONVERSION OF LIGHT NAPHTHA TO ENHANCED VALUE AROMATICS IN AN INTEGRATED REACTOR PROCESS

(71) Applicant: Saudi Arabian Oil Company, Dhahran (SA)

(72) Inventors: Omer Refa Koseoglu, Dhahran (SA); Yaming Jin, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/829,740

(22) Filed: Jun. 1, 2022

(51) Int. Cl.
C07C 6/10 (2006.01)
C07C 7/00 (2006.01)

(52) U.S. Cl.
CPC ............... C07C 6/10 (2013.01); C07C 7/005 (2013.01)

(58) Field of Classification Search
CPC .................................. C07C 6/10; C07C 7/005
See application file for complete search history.

(56) References Cited

U.S. PATENT DOCUMENTS

| | | |
|---|---|---|
| 3,756,942 A | 9/1973 | Camberley |
| 3,953,366 A | 4/1976 | Morrison |
| 4,157,293 A | 6/1979 | Plank et al. |
| 4,190,519 A | 2/1980 | Miller et al. |
| 4,330,396 A | 5/1982 | Miller |
| 4,861,934 A | 8/1989 | Suzuki et al. |
| 5,055,437 A | 10/1991 | Herbst |
| 5,073,673 A | 12/1991 | Hirabayashi et al. |
| 5,276,232 A | 1/1994 | Inoue |
| 5,958,216 A | 9/1999 | Glover |
| 6,177,002 B1 | 1/2001 | Glover |
| 6,190,534 B1 | 2/2001 | Bogdan |
| 7,285,696 B2 | 10/2007 | Schmidt et al. |
| 9,242,233 B2 | 1/2016 | Ghosh et al. |
| 10,308,567 B2 | 6/2019 | Jin et al. |

(Continued)

FOREIGN PATENT DOCUMENTS

CN 106552663 A 4/2017

OTHER PUBLICATIONS

Agaeva et al., "Product Control in Catalytic Aromatization of C2+ Hydrocarbons", Petroleum Chemistry, vol. 47, No. 3, pp. 162-166, 2007.

(Continued)

*Primary Examiner* — Thuan D Dang
(74) *Attorney, Agent, or Firm* — Dinsmore & Shohl LLP

(57) ABSTRACT

An integrated process for conversion of a hydrocarbon stream comprising at least 60% by weight C5-C6 normal paraffins and iso-paraffins to enhanced value aromatics. The process includes passing the hydrocarbon stream through the first reactor, the first reactor being an aromatization reactor with an aromatization catalyst disposed therein to generate an aromatization product stream. The process further includes passing the aromatization product stream through a separator configured to remove C1-C4 gases to generate an aromatic rich stream. The process finally includes passing the aromatic rich stream combined with a reformate effluent fraction from a catalytic reforming unit to an aromatic recovery complex to separate the aromatic rich stream into a benzene fraction, a toluene fraction, a para-xylene fraction, an aromatic bottoms fraction comprising C9+ aromatic hydrocarbons, and a non-aromatics fraction. An associated system for performing the process is also provided.

20 Claims, 6 Drawing Sheets

(56) References Cited

U.S. PATENT DOCUMENTS

| | | | |
|---|---|---|---|
| 10,427,142 | B1 | 10/2019 | Al-Herz et al. |
| 10,519,387 | B2 | 12/2019 | Ravishankar et al. |
| 10,596,558 | B2 | 3/2020 | Arvind et al. |
| 11,021,422 | B1 | 6/2021 | Koseoglu |
| 2004/0011063 | A1 | 1/2004 | Suzuki et al. |
| 2004/0236164 | A1 | 11/2004 | Rangarajan et al. |
| 2011/0132804 | A1 | 6/2011 | Stevenson et al. |
| 2012/0277503 | A1 | 11/2012 | Wegerer et al. |
| 2012/0283494 | A1 | 11/2012 | Smith et al. |
| 2014/0316179 | A1 | 10/2014 | Ghosh et al. |
| 2016/0030931 | A1 | 2/2016 | Kelkar et al. |
| 2017/0088485 | A1 | 3/2017 | Shekyar et al. |
| 2017/0114288 | A1 | 4/2017 | Ravishankar et al. |
| 2017/0144138 | A1 | 5/2017 | Arvind et al. |
| 2017/0305812 | A1 | 10/2017 | Keusenkothen |
| 2018/0066197 | A1 | 3/2018 | Koseoglu et al. |
| 2018/0305273 | A1 | 10/2018 | Patel et al. |
| 2019/0224653 | A1 | 7/2019 | Koseoglu et al. |
| 2020/0025276 | A1 | 1/2020 | Kojima et al. |
| 2020/0407649 | A1 | 12/2020 | Lapinski et al. |

OTHER PUBLICATIONS

Aitani et al., "Catalytic Upgrading of Light Naphtha to Gasoline Blending Components: A Mini Review", Energy & Fuels, vol. 33, pp. 3828-3842, 2019.

Bhan et al., "Propane Aromatization over HZSM-5 and Ga/HZSM-5 Catalysts", Catalysis Reviews, 50:19-151, 2008.

Dicksson et al., "The Future of Petrochemicals: Growth Surrounded by Uncertainty", Deloitte, New York, 2019.

Ellouh et al. "Light Paraffinic Naphtha to BTX Aromatics over Metal-Modified Pt/ZSM-5", Chemistryselect, vol. 5 , No. 44, Nov. 30, 2020, pp. 13807-13813.

Hidalgo et al., Current uses and trends in catalytic isomerization, alkylation and etherification processes to improve gasoline quality, Central European Journal of Chemistry, vol. 12, No. 1, pp. 1-13, 2014.

Hodala et al., "Aromatization of C5-rich Light Naphtha Feedstock over Tailored Zeolite Catalysts: Comparison and Model Compounds (n-C5—n-C7)", ChemPubSoc Europe, Chemistry Select, 1, pp. 2515-2521, 2016.

Knai et al., "Aromatization of N-hexane over ZnOH-ZSM-5 catalysts", Journal of Catalysts, vol. 114, Issue 2, pp. 284-290, Dec. 1988.

Meriaudeau et al., "Dehydrocyclization of Alkanes Over Zeolite-Supported Metal Catalysts: Monofunctional or Bifunctional Route", Catalysts Reviews, vol. 39, pp. 5-48, 1977.

Ogunronbi et al. "New insights into hierarchical metal-containing zeolites; synthesis and kinetic modelling of mesoporous gallium-containing ZSM-5 for propane aromatization" Journal of Molecular Catalysis: A Chemical, vol. 406, pp. 1-18, Sep. 1, 2015.

Ono, "Transformation of Lower Alkanes into Aromatic Hydrocarbons over ZSM-5 Zeolites", Catalysts Reviews, Science and Engineering, vol. 34, pp. 179-226, 1992.

Su et al., "Synergic Effect of GaO+/Bronsted Acid in Hierarchical Ga/Al-ZSM-5 Bifunctional Catalysts for 1-Hexene Aromatization", Industrial & Engineering Chemistry Research, vol. 58, pp. 20543-20552, 2019.

Tamiyakul et al., "Generation of reductive Zn species over Zn/HZSM-5 catalysts for n-pentane aromatization", Applied Catalystis A: General, vol. 525, pp. 190-196, 2016.

Tshabalala et al., "Aromatizatin of n-hexane over Ga, Mo and Zn modified H-ZSM-5 zeolite catalyst", Catalysis Communications, vol. 72, pp. 49-52, 2015.

Tuktin et al. "Catalytic Conversion of Light Hydrocarbons into Aromatic Hydrocarbons over Modified Zeolite Catalysts", Oriental Journal of Chemistry, vol. 33, No. 4, pp. 1799-1804, Aug. 28, 2017.

Verboekend et al., "Full Compositional Flexibility in the Preparatijn of Mesoporous MFI Zeolites by Desilication", The Journal of Physical Chemistry, 48 pgs., 2011.

Wannapakdee et al., "Aromatization of C5 hydrocarbons over Ga-modified hierarchical HZSM-5 nanosheets", Fuel, vol. 236, pp. 1243-1253, 2019.

Youming et al., "Aromatization of Methanol over La/Zn/HZSM-5 Catalysts", Catalysis, Kinetics and Reactors, Chinese Journal of Chemical Engineering, vol. 19, No. 3, pp. 439-445, 2011.

Yu et al., "Alkane Activation Initiated by Hydride Transfer: Co-conversion of Propane and Methanol over H-ZSM-5 Zeolite", Agnew. Chem. Int. Ed. No. 54, pp. 7363-7366, 2015.

CONVERSION OF LIGHT NAPHTHA TO ENHANCED VALUE AROMATICS IN AN INTEGRATED REACTOR PROCESS

TECHNICAL FIELD

The present disclosure relates to an integrated process and associated system for conversion of a hydrocarbon stream comprising C5-C6 normal paraffins and iso-paraffins to enhanced value aromatics.

BACKGROUND

Aromatics such as BTX (benzene, toluene, and xylenes) are valuable chemicals frequently utilized in the production of many materials and formulation of many consumer goods. For example, BTX compounds are frequently utilized during the processing or production of petroleum products and during the production of consumer goods such as paints and lacquers, thinners, fuels, rubber products, adhesives, inks, cosmetics and pharmaceutical products. As such, their plentiful, efficient, and economical production is generally desirable.

The transformation of light naphtha or $C_5$-$C_6$ streams, which originate from refineries and gas plants, into value-added gasoline blending components such as BTX has been an ongoing challenge to researchers in academia and industry. Currently, the global demand for light naphtha is estimated at 378 million tons per year, with an annual growth rate of 1.9%. The primary use for light naphtha is as feed for steam crackers (60%) for the production of olefins (ethylene, propylene, and butenes), and as a blending stock for gasoline production (30%). However, the light naphtha stream has generally become an undesirable gasoline blending component because of its low octane number. This challenge has led refiners to seek novel approaches to upgrade this low-value stream into higher value products.

The transformation of light naphtha has been hindered by inertness of carbon-carbon and carbon-hydrogen bonds, which results in an elevated temperature and, therefore, unfavorable thermodynamics, low selectivity and yields, and high cost for commercial applications. As refiners continue to process lighter feeds, such as shale oil and condensates, a process that cost effectively converts excess $C_5$-$C_6$ components is highly desirable.

SUMMARY

Accordingly, there is a clear and long-standing need to provide an efficient and economical process for the production of value added aromatics, and more particularly benzene and xylene, from a feedstock comprising substantial quantities of light naphtha and in particular normal paraffins and iso-paraffins having 5 or 6 carbon atoms.

In accordance with one or more embodiments of the present disclosure, an integrated process for conversion of a hydrocarbon stream comprising C5-C6 normal paraffins and iso-paraffins to enhanced value aromatics is disclosed. The process includes (i) providing the hydrocarbon stream comprising at least 60% by weight C5-C6 normal paraffins and iso-paraffins to a first reactor; (ii) passing the hydrocarbon stream through the first reactor, the first reactor being an aromatization reactor with an aromatization catalyst disposed therein to generate an aromatization product stream; (iii) passing the aromatization product stream from the first reactor through a separator, the separator configured to remove C1-C4 gases from the aromatization product stream to generate an aromatic rich stream; and (iv) passing the aromatic rich stream to an aromatic recovery complex to separate the aromatic rich stream into a benzene fraction, a toluene fraction, a para-xylene fraction, an aromatic bottoms fraction comprising C9+ aromatic hydrocarbons, and a non-aromatics fraction. Further, a reformate effluent fraction from a catalytic reforming unit is combined with the aromatization product stream prior to passing the aromatization product stream to the separator or is combined with the aromatic rich stream prior to passage to the aromatic recovery complex.

In additional embodiments, the process further includes passing the toluene fraction from the aromatic recovery complex through a transalkylation reactor with a transalkylation catalyst disposed therein to generate a transalkylation effluent stream comprising xylene and benzene through a disproportionation reaction of toluene in the toluene fraction and then passing the transalkylation effluent stream through the separator or directly to a component of the aromatic recovery complex.

In yet further embodiments, the separator additionally separates the aromatic rich stream to generate a C5-C6 stream, a toluene stream, and a C8+ stream; wherein the toluene stream is passed to the transalkylation reactor, the C5-C6 stream is passed to the aromatic recovery complex, and the C8+ stream is passed to the aromatic recovery complex.

Additional features and advantages of the described embodiments will be set forth in the detailed description that follows. The additional features and advantages of the described embodiments will be, in part, readily apparent to those skilled in the art from that description or recognized by practicing the described embodiments, including the detailed description that follows as well as the drawings and the claims.

BRIEF DESCRIPTION OF THE DRAWINGS

The following detailed description of specific embodiments of the present disclosure can be best understood when read in conjunction with the following drawings in which.

Reference will now be made in greater detail to various embodiments, some embodiments of which are illustrated in the accompanying drawings. Whenever possible, the same

DETAILED DESCRIPTION

Reference will now be made in detail to embodiments of an integrated process and associated system for conversion of a hydrocarbon stream comprising C5-C6 normal paraffins and iso-paraffins to enhanced value aromatics in accordance with the present disclosure. While the system for conversion of a hydrocarbon stream C5-C6 normal paraffins and iso-paraffins to enhanced value aromatics of FIGS. 1, 2 and 3 are provided as exemplary, it should be understood that the present systems and methods may encompass other configurations.

The processes and systems of the present disclosure provide increased conversion of light naphtha feedstock to enhanced value products such as benzene, toluene, and xylenes (BTX). And more specifically benzene and para-xylene. Specifically, the processes and systems of the present disclosure incorporate an aromatization procedure to aromatize the hydrocarbon feedstock in an initial processing step before passage of the resulting product stream to further unit operations for integration with a reformate effluent fraction from a catalytic reforming unit for conversion and separation of the combined stream as enhanced value products such as BTX. The processes and systems may also be specifically configured to preferentially generate benzene and para-xylene product stream.

Figure 1:
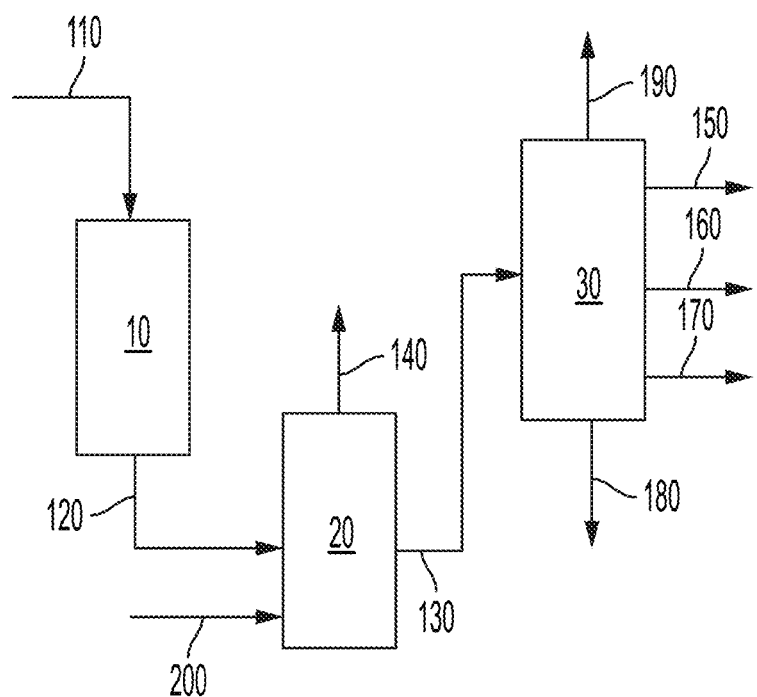
FIG. 1 is a schematic illustration of one or more embodiments of the integrated refinery process of the present disclosure.

In one or more embodiments and generally with reference to FIG. 1, an integrated process for conversion of a hydrocarbon stream to enhanced value aromatics includes providing a hydrocarbon stream 110 comprising C5-C6 normal paraffins and iso-paraffins to a first reactor 10. Generally, the hydrocarbon stream 110 comprises at least 60% by weight of normal paraffins and iso-paraffins having 5 or 6 carbon atoms. The hydrocarbon stream 110 comprising C5-C6 normal paraffins and iso-paraffins is passed through the first reactor 10 to generate an aromatization product stream 120 comprising aromatics. As such, the first reactor 10 is an aromatization reactor an aromatization catalyst disposed therein to generate the aromatization product stream 120. The aromatization product stream 120 from the first reactor 10 is subsequently passed through a separator 20 to remove C1-C4 gases 140 from the aromatization product stream 120 to generate an aromatic rich stream 130. Finally, the aromatic rich stream 130 is passed to an aromatic recovery complex 30 to separate the aromatic rich stream 130 into a benzene fraction 150, a toluene fraction 160, a para-xylene fraction 170, an aromatic bottoms fraction 180 comprising C9+ aromatic hydrocarbons, and a non-aromatics fraction 190 comprising the non-aromatic products. Further, a reformate effluent fraction 200 from a catalytic reforming unit is combined with the aromatization product stream 120 prior to passing the aromatization product stream 120 to the separator 20 as illustrated in FIG. 1 or is combined with the aromatic rich stream 130 prior to passage to the aromatic recovery complex 30 as illustrated in FIG. 2.

Figure 2:
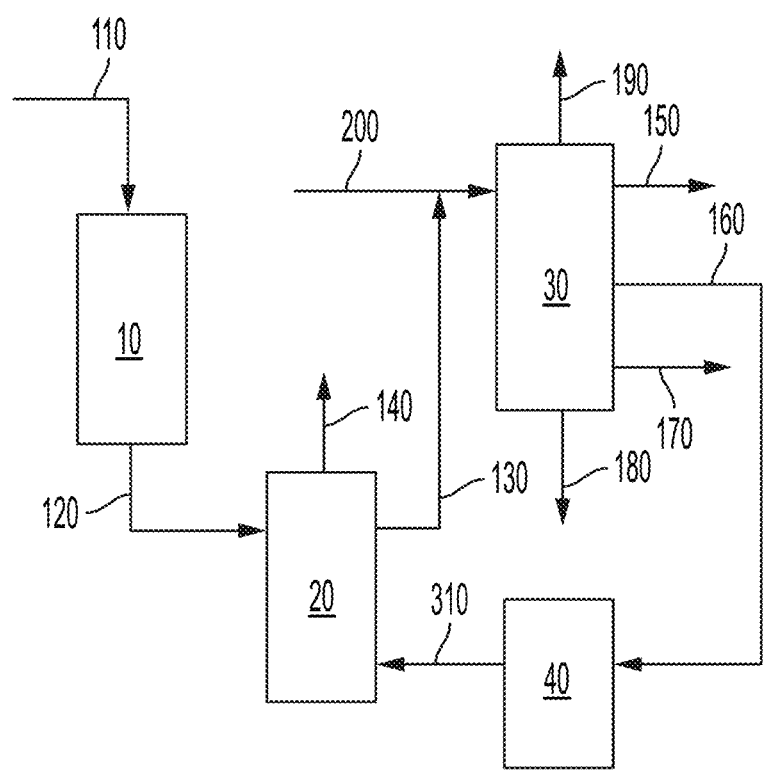
FIG. 2 is a schematic illustration of one or more embodiments of the integrated refinery process of the present disclosure including a transalkylation reactor.
Figure 3:
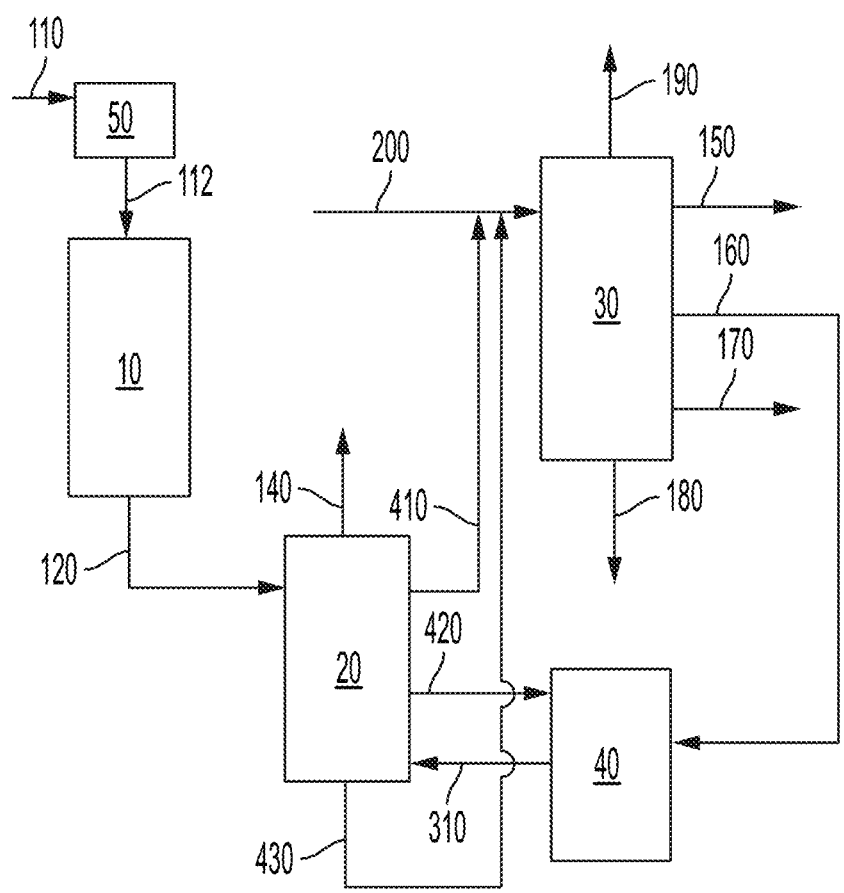
FIG. 3 is a schematic illustration of one or more embodiments of the integrated refinery process of the present disclosure including a transalkylation reactor and separation of the aromatic rich stream.

In one or more further embodiments and generally with reference to FIG. 2, an integrated process for conversion of a hydrocarbon stream to enhanced value aromatics includes additionally includes a transalkylation reactor 40 having a transalkylation catalyst disposed therein to generate a transalkylation effluent stream 310 comprising xylene and benzene through a disproportionation reaction of toluene in the toluene fraction 160. Specifically, the integrated process for conversion of a hydrocarbon stream to enhanced value aromatics includes providing a hydrocarbon stream 110 comprising C5-C6 normal paraffins and iso-paraffins to a first reactor 10 where the hydrocarbon stream 110 generally comprises at least 60% by weight of normal paraffins and iso-paraffins having 5 or 6 carbon atoms. The hydrocarbon stream 110 comprising C5-C6 normal paraffins and iso-paraffins is passed through the first reactor 10 to generate an aromatization product stream 120 comprising aromatics. As such, the first reactor 10 is an aromatization reactor an aromatization catalyst disposed therein to generate the aromatization product stream 120. The aromatization product stream 120 from the first reactor 10 is subsequently passed through a separator 20 to remove C1-C4 gases 140 from the aromatization product stream 120 to generate an aromatic rich stream 130. Finally, the aromatic rich stream 130 is passed to an aromatic recovery complex 30 to separate the aromatic rich stream 130 into a benzene fraction 150, a toluene fraction 160, a para-xylene fraction 170, an aromatic bottoms fraction 180 comprising C9+ aromatic hydrocarbons, and a non-aromatics fraction 190 comprising the non-aromatic products. Further, the toluene fraction 160 from the aromatic recovery complex 30 is passed through the transalkylation reactor 40 with the transalkylation catalyst disposed therein to generate the transalkylation effluent stream 310 comprising xylene and benzene through a disproportionation reaction of toluene in the toluene fraction 160. The transalkylation effluent stream 310 is then passed through the separator 20 such that the transalkylation effluent stream 310 is combined with the aromatic rich stream 130. The transalkylation effluent stream 310 may alternatively be passed directly to a component of the aromatic recovery complex. A reformate effluent fraction 200 from a catalytic reforming unit is then combined with the aromatic rich stream 130 prior to passage to the aromatic recovery complex 30 such that the combined aromatic rich stream 130 and reformate effluent fraction 200 are processed in the aromatic recovery complex 30.

In one or more further embodiments and generally with reference to FIG. 3, an integrated process for conversion of a hydrocarbon stream to enhanced value aromatics includes additionally separating the aromatization product stream 120 to generate a C5-C6 stream 410 which includes benzene, a toluene stream 420, and a C8+ stream 430 in addition to the C1-C4 gases 140. As such, the toluene stream 420 may be provided to a transalkylation reactor 40 having a transalkylation catalyst disposed therein to generate a transalkylation effluent stream 310 comprising xylene and benzene through a disproportionation reaction of toluene in the toluene fraction 160. Specifically, the integrated process for conversion of a hydrocarbon stream to enhanced value aromatics includes providing a hydrocarbon stream 110 comprising C5-C6 normal paraffins and iso-paraffins to a first reactor 10 where the hydrocarbon stream 110 generally comprises at least 60% by weight of normal paraffins and iso-paraffins having 5 or 6 carbon atoms. The hydrocarbon stream 110 comprising C5-C6 normal paraffins and iso-paraffins is passed through the first reactor 10 to generate an aromatization product stream 120 comprising aromatics. As such, the first reactor 10 is an aromatization reactor an aromatization catalyst disposed therein to generate the aromatization product stream 120. The aromatization product stream 120 from the first reactor 10 is subsequently passed through a separator 20 to remove C1-C4 gases 140 from the aromatization product stream 120 and generate the C5-C6 stream 410 comprising benzene, the toluene stream 420, and the C8+ stream 430. Finally, the C5-C6 stream 410 comprising benzene and the C8+ stream 430 along with a reformate effluent fraction 200 from a catalytic reforming unit are passed to an aromatic recovery complex 30 to separate the combined streams into a benzene fraction 150, a toluene fraction 160, a para-xylene fraction 170, an aromatic bottoms fraction 180 comprising C9+ aromatic hydrocarbons, and a non-aromatics fraction 190 comprising the non-aromatic products. Further, the toluene fraction 160 from the aromatic recovery complex 30 is passed along with the toluene stream 420 through the transalkylation reactor 40 with the transalkylation catalyst disposed therein to generate the transalkylation effluent stream 310 comprising xylene and benzene. The transalkylation effluent stream 310 is then passed through the separator 20 such that the transalkylation effluent stream 310 is combined with the C5-C6 stream 410. The transalkylation effluent stream 310 may alternatively be passed directly to a component of the aromatic recovery complex.

Having disclosed the basic operation of the integrated process for conversion of a hydrocarbon stream comprising C5-C6 normal paraffins and iso-paraffins to enhanced value aromatics, each step of the embodiments of the integrated process is now provided in further detail.

Hydrocarbon Feed

The hydrocarbon stream 110 comprises light naphtha. For purposes of this disclosure, light naphtha is considered to be paraffinic hydrocarbons containing 5 or 6 carbon atoms. Light naphtha generally has a boiling point range of 90 to 200° F. (approximately 32.2 to 93.3° C.). It is noted that the boiling points of n-pentane and n-hexane are 36° C. and 69° C. respectively. However in a refinery, due to inefficient separation, there may carried over material in a light naphtha stream resulting in a limited amount of higher carbon number molecules as well. Specifically, depending on the source of light naphtha, cut-points, and reactor efficiency, a light naphtha stream may be composed of normal paraffins and iso-paraffins along with a minority percentage of normal and iso-olefins, saturated and unsaturated naphthenes, and even small portion of aromatic compounds such as benzene and toluene. However, for clarity the hydrocarbon stream 110 as discussed in the present disclosure is explicitly indicated as comprising at least 60% by weight of normal paraffins and iso-paraffins having 5 or 6 carbon atoms. It will be appreciated that preference is given to iso-paraffins as such species are preferred for aromatization.

In various embodiments, the hydrocarbon stream 110 may comprise normal paraffins and iso-paraffins from various sources including crude oil, gas condensate, coal liquid, bio fuels, intermediate refinery processes, and their combinations. The intermediate refinery processes may include hydrocracking, hydrotreating, delayed coking, visbreaking, fluid catalytic cracking, and effluent of a residue hydroprocessing unit.

In one or more embodiments, the hydrocarbon stream 110 comprises at least 60% by weight of normal paraffins and iso-paraffins having 5 or 6 carbon atoms. In various further embodiments, the hydrocarbon stream 110 comprises at least 75% by weight, at least 78% by weight, at least 80% by weight, at least 90% by weight, at least 95% by weight, or at least 98% by weight of normal paraffins and iso-paraffins having 5 or 6 carbon atoms. Each such range is capped at 100% by weight of normal paraffins and iso-paraffins having 5 or 6 carbon atoms. In one or more embodiments, the hydrocarbon stream 110 consists essentially of normal paraffins and iso-paraffins having 5 or 6 carbon atoms. The elevated level of paraffins in the hydrocarbon stream 110 provides ample reactants for conversion to enhanced value products including BTX.

Aromatization Reactor

In one or more embodiments, the first reactor 10 may be an aromatization reactor with an aromatization catalyst disposed therein to generate the aromatization product stream 120. In accordance with the system configuration as illustrated in FIGS. 1, 2, and 3, the hydrocarbon stream 110 comprising C5-C6 normal paraffins and iso-paraffins is converted to the aromatization product stream 120 in the first reactor 10. The catalytic bed reactor of the first reactor 10 may operate as a fixed bed reactor in one or more embodiments. In further embodiments, the catalytic bed reactor of the first reactor 10 may operate as a moving bed reactor.

The aromatization catalyst may be selected to efficiently aromatize the feed stream to the first reactor 10. Specifically, aromatization catalyst may be selected to efficiently aromatize the hydrocarbon stream 110 comprising C5-C6 normal paraffins and iso-paraffins. It will be appreciated that the aromatization catalyst may be selected to optimize performance based on the specific composition of the hydrocarbon stream 110.

In accordance with various embodiments, the aromatization catalyst may include a metal oxide component dispersed on the surfaces of the zeolite support. The metal oxide component may include one or more oxides of metal elements selected from groups 4 to 13 of the International Union of Pure and Applied Chemistry (IUPAC) periodic table, such as groups 8 to 13 of the IUPAC periodic table. In one or more embodiments, the metal element of the one or more metal oxides may be a metal element selected from groups 4 to 13 and periods 4 to 6 of the IUPAC periodic table, such as period 4 of the periodic table. The metal element of the metal oxide may include, but is not limited to, titanium, vanadium, chromium, manganese, iron, cobalt, nickel, copper, zinc, gallium, molybdenum, palladium, silver, hafnium, tungsten, platinum, gold, or combinations of these metal elements. In one or more embodiments, the metal element of the one or more metal oxides may include gallium, zinc, iron, hafnium, or combinations of these metals. In one or more embodiments, the metal oxide may be gallium oxide.

In one or more embodiments the aromatization catalyst may comprise a gallium modified H-MFI type zeolite. Specifically, the aromatization catalyst may comprise a catalyst formed from gallium incorporated into a H-MFI type zeolite. Such a catalyst may comprise from 1 to 5 weight percent gallium (Ga) based on the total catalyst. For example, in various embodiments, the gallium modified H-MFI type zeolite catalyst may comprise from 1 to 4 weight percent gallium, 1 to 3 weight percent gallium, 1.5 to 2.5 weight percent gallium, 1.8 to 2.2 weight percent gallium, or approximately 2 weight percent gallium. It will be appreciated that integration of gallium at other ratios encompassed by the broadest ranges are also envisioned but not explicitly delineated for brevity. As previously indicted, in various embodiments, the gallium may be substituted with an alternative metal element while maintaining the remaining parameters of the disclosed gallium modified H-MFI type zeolite. In various embodiments, the silica to alumina ratio of the H-MFI type zeolite may vary from 20 to 100, 20 to 80, 20 to 50, or 20 to 30.

In one or more embodiments and in accordance with the various configurations, the hydrocarbon stream may be provided to the first reactor 10 serving as the aromatization reactor at a weight hourly space velocity (LHSV) of 0.1 to 10 $h^{-1}$. In various further embodiments, the hydrocarbon stream 110 is provided to the first reactor 10 at a LHSV of 0.1 to 8 $h^{-1}$, 0.3 to 10 $h^{-1}$, 0.5 to 5 $h^{-1}$, 0.8 to 3 $h^{-1}$, 0.8 to 2 $h^{-1}$, or approximately 1 $h^{-1}$. It will be appreciated that greater LHSV results in lower aromatics yield while lesser LHSV favors formation of less desirable heavy aromatics.

In one or more embodiments and in accordance with the various configurations, the first reactor 10 serving as the aromatization reactor may be operated at a reaction temperature of 500 to 600° C. In various embodiments, the second reactor 20 may be operated at a reaction temperature of 500 to 575° C., 525 to 600° C., 525 to 575° C., or approximately 550° C. It will be appreciated that lesser temperature leads to lesser conversion while greater temperature results in faster catalyst deactivation.

In one or more embodiments and in accordance with the various configurations, the first reactor 10 may be operated at a pressure of 0.5 to 10 bar, 0.5 to 5 bar, 0.9 to 3 bar, or approximately 1 bar. It will be appreciated that lesser pressure favors aromatization reaction, but a minimum level of positive pressure is needed for practical operation.

Separator

In one or more embodiments, the aromatization product stream 120 from the first reactor 10 is passed through a separator 20. The separator 20 is configured to remove C1-C4 gases from the aromatization product stream 120 to generate the aromatic rich stream 130.

In various embodiments, the separator 20 may comprise any separation device that at least partially separates one or more chemicals that are mixed in a process stream from one another. For example, the separator 20 may selectively separate differing chemical species from one another, forming one or more chemical fractions. Examples of separators 20 include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure with regards to the separator 20 may not completely separate all of one chemical constituent from all of another chemical constituent. It should be understood that the separation processes described in this disclosure "at least partially" separate different chemical components from one another, and that even if not explicitly stated, it should be understood that separation may include only partial separation. However, even if not explicitly stated, it should be understood that separation may include complete separation in one or more embodiments as well.

It should be additionally understood that where only one separator 20 is depicted in a figure or described, two or more separators 20 may be employed to carry out the identical or substantially identical separation. For example, where a separator 20 with multiple outlets is described or illustrated, it is contemplated that several separators 20 arranged in series may equally separate the feed or feeds to the separator 20 and such embodiments are within the scope of the presently described embodiments. The separator 20 may include one or more distillation units. The distillation units may include an atmospheric distillation unit, a vacuum distillation unit, or both.

In one or more embodiments and with reference to FIGS. 1 and 2, the separator 20 merely removes C1-C4 gases 140 from any feeds to the separator 20 with the remainder passed to the aromatic recovery complex 30. Aromatic recovery complexes are designed to receive liquid stream so removal of the C1-C4 stream stabilizes the feed stream to the aromatic recovery complex. It will be appreciated that removal of the C1-C4 gases 140 also allows for the C1-C4 gases 140 to be collected and directly utilized as value added products or further processed into value added products. For example, the C1-C4 gases 140 can be used as a fuel gas or further separated into dry gas (C1-C2) and LPG (C2-C4) or separated into fuel gas as C1 and C2-C4 as a feedstock to steam crackers. Further, removal of the C1-C4 gases 140 reduces the burden on the aromatic recovery complex 30.

In one or more embodiments and with reference to FIG. 3, the separator 20 removes C1-C4 gases 140 from any feeds to the separator 20, but also additionally separates any feeds to the separator 20 to generate the C5-C6 stream 410 which includes benzene, the toluene stream 420, and the C8+ stream 430. It will be appreciated that removal of the C1-C4 gases 140 once again allows for the C1-C4 gases 140 to be collected and directly utilized as value added products or further processed into value added products. However, the further separation to generate the C5-C6 stream 410 comprising benzene, the toluene stream 420, and the C8+ stream 430 allows transfer of toluene in the toluene stream 420 directly to the transalkylation reactor 40, if present, for immediate processing without necessitating passage through the aromatic recovery complex 30. It will be appreciated that in accordance with such arrangement, the C5-C6 stream 410 which includes benzene and the C8+ stream 430 in combination replace the aromatic rich stream 130. As such, any indication of the aromatic rich stream 130 being provided to a unit or processed in any manner additionally includes embodiments where the C5-C6 stream 410 and the C8+ stream 430 in combination are provided to the unit or processed in the same manner.

Figure 4:
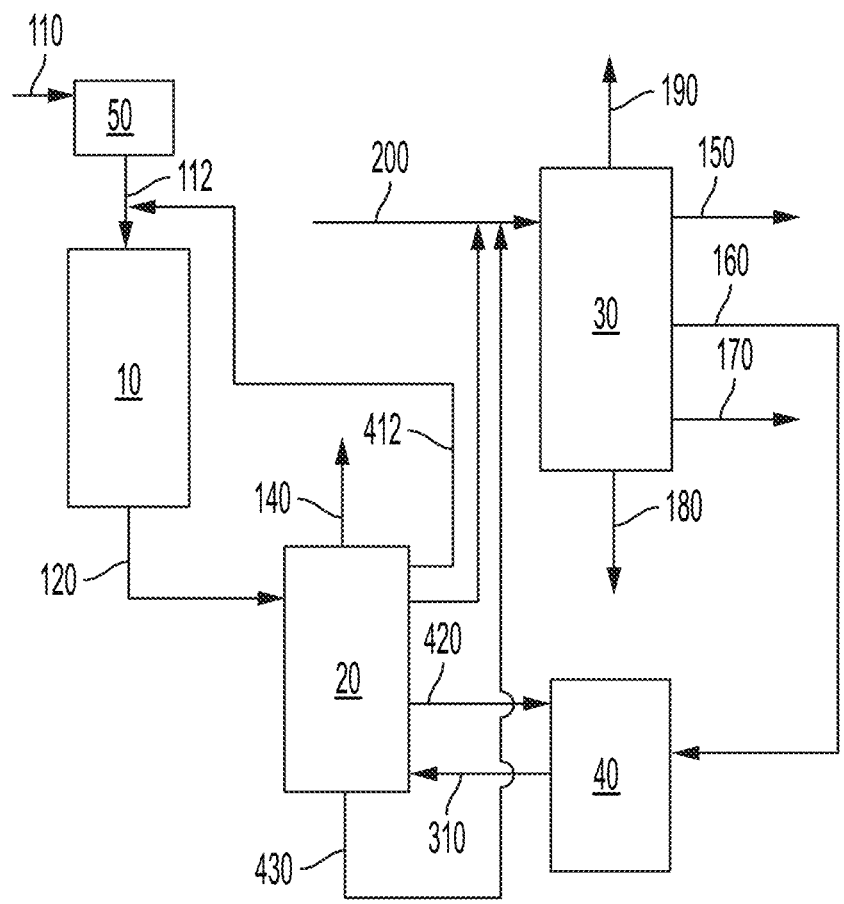
FIG. 4 is a schematic illustration of one or more embodiments of the integrated refinery process of the present disclosure including separation of the C4-C5 stream into the C4-C5 non-aromatic stream and the C4-C5 aromatic stream.

In one or more embodiments and with reference to FIG. 4, the separator 20 removes C1-C4 gases 140 from any feeds to the separator 20, separates any feeds to the separator 20 to generate the toluene stream 420, and the C8+ stream 430, and additionally separates the feeds to the separator 20 to generate a C5-C6 non-aromatic stream 412 and a C5-C6 aromatic stream 414. Such further separation of the components in the C5-C6 stream 410 into the separate C5-C6 non-aromatic stream 412 and C5-C6 aromatic stream 414 allows for the C5-C6 non-aromatic stream 412 to be further processed and aromatized in the first reactor 10 serving as an aromatization reactor. It will be appreciated that in accordance with such arrangement, the C5-C6 aromatic stream 414 replaces the C5-C6 stream 410 provided to the aromatic rich stream 130. As such, any indication of the aromatic rich stream 130 or C5-C6 stream 410 being provided to a unit or processed in any manner additionally includes embodiments where the C5-C6 aromatic stream 414 is provided to the unit or processed in the same manner.

With reference to FIG. 1, in one or more embodiments, the separator 20 may include a simple flash column with no theoretical plates or a stripper with a gas or a steam or a single fractionation column with at least 15 theoretical trays or may include a plurality of atmospheric distillation units, vacuum distillation units, or both, which may be operated in series or in parallel to separate the aromatization product stream 120 into the aromatic rich stream 130 and the C1-C4 gases 140.

With reference to FIG. 2, in one or more embodiments, the separator 20 may include a simple flash column with no theoretical plates or a stripper with a gas or a steam or a single fractionation column with at least 15 theoretical trays or may include a plurality of atmospheric distillation units, vacuum distillation units, or both, which may be operated in series or in parallel to separate the combined feeds of the aromatization product stream 120 and the transalkylation effluent stream 310 into the aromatic rich stream 130 and the C1-C4 gases 140.

With reference to FIG. 3, in one or more embodiments, the separator 20 may include a simple flash column with no theoretical plates or a stripper with a gas or a steam or a single fractionation column with at least 15 theoretical trays or may include a plurality of atmospheric distillation units, or both, which may be operated in series or in parallel to separate the combined feeds of the aromatization product stream 120 and the transalkylation effluent stream 310 into the C5-C6 stream 410, the toluene stream 420, the C8+ stream 430, and the C1-C4 gases 140.

With reference to FIG. 4, in one or more embodiments, the separator 20 may include a simple flash column with no theoretical plates or a stripper with a gas or a steam or a single fractionation column with at least 15 theoretical trays or may include a plurality of atmospheric distillation units, vacuum distillation units, or both, which may be operated in series or in parallel to separate the combined feeds of the aromatization product stream 120 and the transalkylation effluent stream 310 into the C5-C6 non-aromatic stream 412, the C5-C6 aromatic stream 414, the toluene stream 420, the C8+ stream 430, and the C1-C4 gases 140.

In various embodiments, the separator 20 may obtain cuts of the hydrocarbon feed streams to the separator 20 within +/−5° C., +/−4° C., +/−3° C., or +/−2° C. Further, the pressure within the separator 20 is typically in the range of 1 to 3 bars. However, if the feed to the separator 20 is coming from a reactor with higher pressure, the separator 20 may be divided into at least a high pressure separator and a subsequent low pressure separator.

Aromatic Recovery Complex

In one or more embodiments, the aromatic rich stream 130 is passed to the aromatic recovery complex 30 to separate the aromatic rich stream 130 into the benzene fraction 150, the toluene fraction 160, the para-xylene fraction 170, the aromatic bottoms fraction 180 comprising C9+ aromatic hydrocarbons, and the non-aromatics fraction 190 comprising the non-aromatic components of the aromatic rich stream 130.

Various systems and techniques may be utilized in the aromatic recovery complex 30 for separating the aromatic rich stream 130 into various fractions and the present disclosure is not intended to be limited in nature to the specific arrangement of the aromatic recovery complex 30. Generally, the aromatic recovery complex 30 produces the benzene fraction 150, the toluene fraction 160, the para-xylene fraction 170, the aromatic bottoms fraction 180. Further, while the non-aromatics fraction 190 is illustrated as a single stream for reduced complexity in FIGS. 1, 2, and 3, it will be appreciated that the non-aromatics fraction 190 may be further separated into individual steams of various constituent components. Similarly, while the aromatic bottoms fraction 180 is illustrated as a single stream for reduced complexity in FIGS. 1, 2, and 3, it will be appreciated that the aromatic bottoms fraction 180 may be further separated into individual steams of various constituent components.

There are many configurations of aromatic recovery complexes in general. In one or more embodiments, the aromatic recovery complex 30 may include, for example, a dehexanizer distillation column that removes lighter components and discharges a bottoms product stream. The bottoms product stream may be fed to a benzene distillation column that removes benzene overhead and discharges a bottoms stream having, for example, toluene, mixed xylenes, ethyl benzene, and C9+ aromatic compounds. In some instances, the overhead discharge may enter absorber and stripper columns to purify the benzene. The bottoms stream from the benzene distillation column may be processed in absorber and stripper columns to remove light components and further in distillation columns. The aforementioned absorber and stripper columns may involve solvent extraction.

This bottoms stream from the benzene distillation column may ultimately be processed in distillation columns to separate and recover toluene and various mixed xylenes. The distillation columns may include a toluene distillation column(s) and a xylene distillation column(s). A toluene distillation column may separate and discharge toluene overhead. The xylene distillation column may receive the bottoms discharge from the toluene distillation column, separate and discharge mixed xylenes overhead and discharge a heavy aromatics (C9+) bottoms stream, such as the aromatic bottoms fraction 170.

Figure 6:
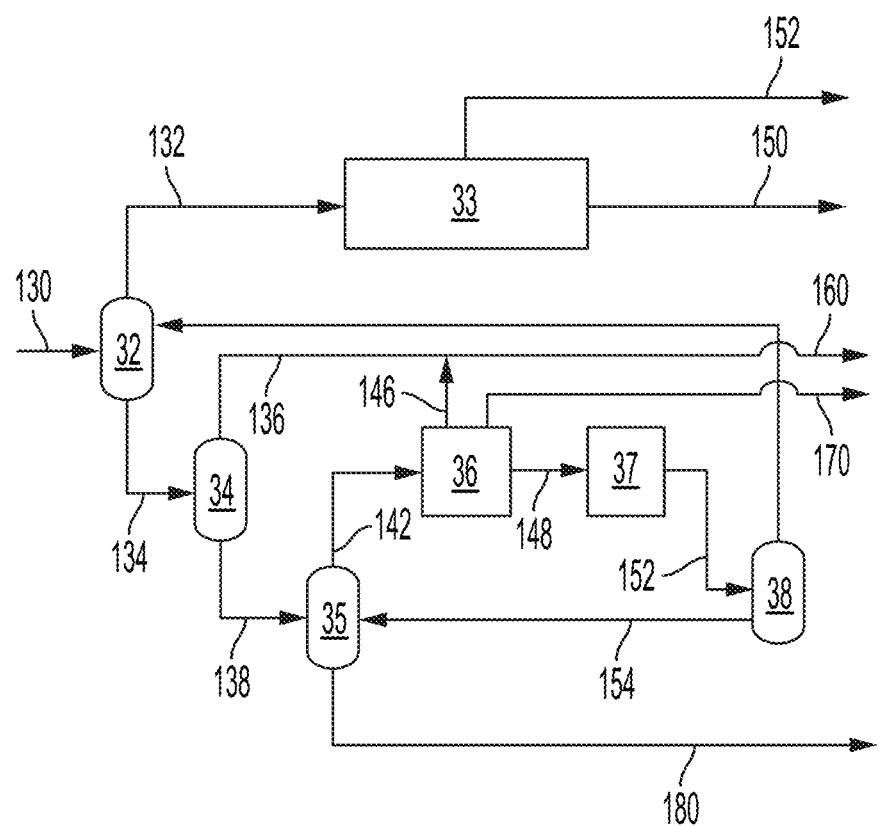
FIG. 6 is a generalized schematic diagram of an aromatics recovery complex.

Referring to FIG. 6, a schematic of an example aromatics recovery complex 30 is shown. The aromatic rich stream 130, which as previously indicated can alternatively be or include one or more of the reformate effluent fraction 200 from a catalytic reforming unit, the C5-C6 stream 410, the C5-C6 aromatic stream 414, and the C8+ stream 430, can be split into two fractions: light reformate stream 132 with C5-C6 hydrocarbons and heavy reformate stream 134 with C7+ hydrocarbons. A reformate splitter 32 can separate aromatic rich stream 130. The light reformate stream 132 can be sent to a benzene extraction unit 33 to extract the benzene as the benzene fraction 150, and to recover substantially benzene-free gasoline in raffinate motor gasoline (mogas) stream 152. The heavy reformate stream 134 can be sent to a splitter 34 which produces a C7 cut mogas stream 136 and a C8+ hydrocarbon stream 138.

Still referring to FIG. 6, a xylene rerun unit 35 can separate C8+ hydrocarbons into C8 hydrocarbon stream 142 and aromatic bottoms fraction 180 comprising C9+ aromatic hydrocarbons. C8 hydrocarbon stream 142 can proceed to p-xylene extraction unit 36 to recover p-xylene in para-xylene fraction 170. P-xylene extraction unit 36 can produce a C7 cut mogas stream 146, which can be combined with C7 cut mogas stream 136 to produce the toluene fraction 160. Other xylenes can be recovered and can be sent to xylene isomerization unit 37 by stream 148 to convert xylenes in stream 148 to p-xylene. The isomerized xylenes can be sent to splitter 38 by stream 152. The converted fraction can be recycled back to p-xylene extraction unit 150 from splitter 162 by way of streams 154 and 142. Splitter top stream 156 can be recycled back to reformate splitter 32.

Transalkylation Reactor

In one or more embodiments, the transalkylation reactor 40 has a transalkylation catalyst disposed therein to generate the transalkylation effluent stream 310 comprising xylene and benzene through a disproportionation reaction of toluene. The catalytic bed reactor of the transalkylation reactor 40 may operate as a fixed bed reactor in one or more embodiments. In further embodiments, the catalytic bed reactor of the transalkylation reactor 40 may operate as a moving bed reactor.

The transalkylation catalyst may be selected to efficiently convert toluene to xylene and benzene via transalkylation and disproportionation. In accordance with various embodiments, the transalkylation catalyst may catalyst comprises at least one catalyst selected from the group consisting of: Beta zeolite; IMF zeolite; ITH zeolite; MFI zeolite; MOR zeolite; MWW zeolite; NES zeolite; Rhenium metal; and a TUN zeolite. Further, the transalkylation catalyst, in one or more embodiments, comprises at least one catalyst active phase metal including a noble metal or a rare earth metal.

The feed to the transalkylation reactor 40 may comprise one or both of the toluene fraction 160 from the aromatic recovery complex 30 and the toluene stream 420 from the separator 20. With reference to FIG. 2, an arrangement is shown where the feed to the transalkylation reactor 40 is exclusively the toluene fraction 160 from the aromatic recovery complex 30. With reference to FIG. 3, an arrangement is shown where the feed to the transalkylation reactor 40 includes both the toluene fraction 160 from the aromatic recovery complex 30 and the toluene stream 420 from the separator 20.

Figure 5:
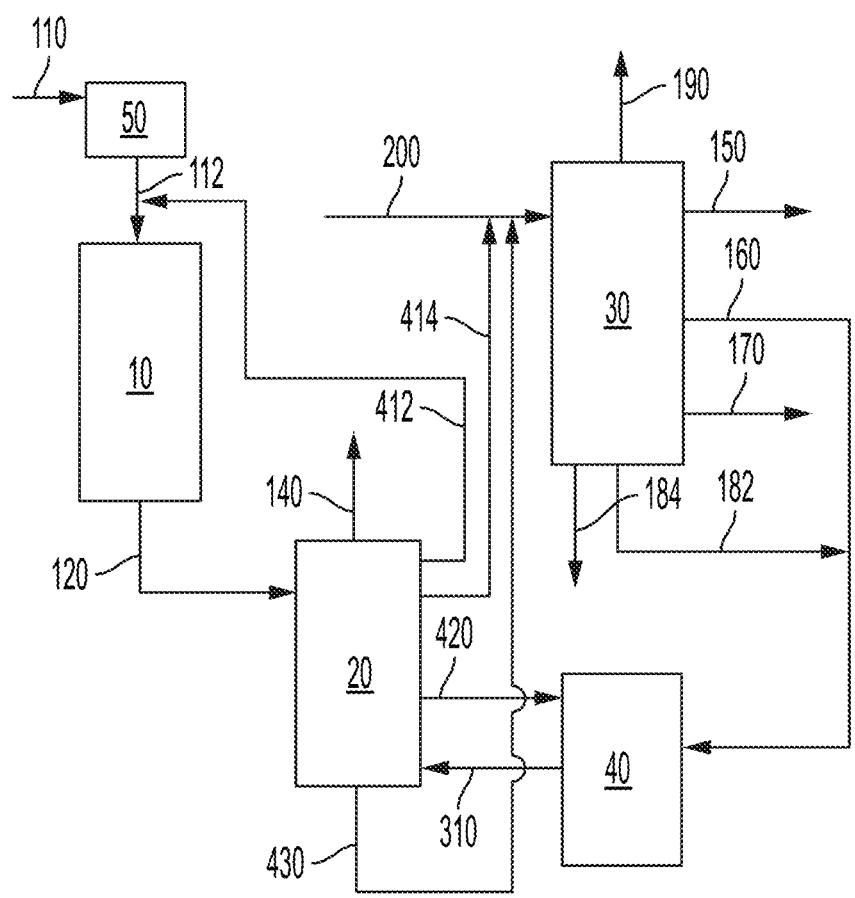
FIG. 5 is a schematic illustration of one or more embodiments of the integrated refinery process of the present disclosure including separation of the aromatic bottoms fraction into the C9-C10 fraction and the C11+ fraction.

In one or more further embodiments and with reference to FIG. 5, the aromatic bottoms stream 180 may be split into a C9-C10 fraction 182 and a C11+ fraction 184. The C9-C10 fraction 182 may then be provided to the transalkylation reactor 40 along with the toluene fraction 160.

It will be appreciated that the flow rate of toluene to the transalkylation reactor 40 is dependent on the composition and flow rate of the hydrocarbon stream 110 and the composition and flow rate of the reformate effluent fraction 200 from a catalytic reforming unit. Regardless, to fully process the toluene directed to the transalkylation reactor 40, in one or more embodiments and in accordance with the various configurations, the total toluene provided to the transalkylation reactor 40 via the various feed stream may be at a liquid space velocity (LHSV) of 1 to 3 $h^{-1}$. It will be appreciated that the reaction for conversion of toluene to benzene, xylenes, ethylbenzene, and other alkylated benzenes is an equilibrium reaction so a greater or lesser LHSV shifts the equilibrium and results in differing product distributions.

In one or more embodiments and in accordance with the various configurations, the transalkylation reactor 40 may be operated at a reaction temperature of 400 to 450° C.

In one or more embodiments and in accordance with the various configurations, the transalkylation reactor 40 may be operated at a pressure of 25 to 35 bar.

It will be appreciated that the xylene products balance may be shifted toward para-xylene by preferentially removing para-xylene and allowing the thermodynamic equilibrium to rebalance to generate additional para-xylene. Further, selection of the transalkylation catalyst to represent a para-selective catalyst which makes a xylene product containing a greater than thermodynamic equilibrium ratio of para-xylene to ortho- and meta-xylene may also shift the products to greater para-xylene production. In one or more embodiments, the toluene fraction 160 is substantially entirely converted to p-xylene.

In one or more embodiments, the transalkylation effluent stream 310 comprising xylene and benzene generated from the disproportionation reaction of toluene is passed to the separator 20. Provision of the transalkylation effluent stream 310 to the separator 20 combines the xylene and benzene generated from the disproportionation reaction of toluene with the aromatization product stream 120 for fractionation and processing in the aromatic recovery complex 30. In embodiments where the separator 20 generates a single aromatic rich stream 130, with reference to FIG. 2, the separator removes any C1-C4 gases 140 from the transalkylation effluent stream 310 and passes the reminder to the aromatic recovery complex 30 as part of the aromatic rich stream 130. With reference to FIG. 3, in embodiments where the separator 20 additionally separates the aromatic rich stream 130 to generate the C5-C6 stream 410, the toluene stream 420, and the C8+ stream 430, the separator additionally removes residual toluene present in the transalkylation effluent stream 310 for immediate reprocessing in the transalkylation reactor 40 before the reminder to the aromatic recovery complex 30 as part of the C5-C6 stream 410 and the C8+ stream 430.

In one or more embodiments, the transalkylation effluent stream 310 comprising xylene and benzene generated from the disproportionation reaction of toluene is passed to directly to the aromatic recovery complex 30. Specifically, in various embodiments, the transalkylation effluent stream 310 is passed to the splitter 34 or the xylene rerun unit 35 of the aromatic recovery complex 30.

Reformate Effluent Fraction

In one or more embodiments, the reformate effluent fraction 200 from the catalytic reforming unit comprises at least 70 wt. % aromatics. In various further embodiments, the reformate effluent fraction 200 from the catalytic reforming unit comprises at least 72 wt. %, at least 75 wt. %, at least 78 wt. %, or at least 80 wt. % aromatics. A non-limiting example composition of the reformate effluent fraction 200 is 4.5 wt. % n-paraffins, 11.5 wt. % iso-paraffins, 1.2 wt. % olefins, 0.5 wt. % naphthenes, and 82.3 wt. % aromatics.

In one or more embodiments, the reformate effluent fraction 200 has a maximum olefin content of 3 wt. %. The olefins present in the reformate effluent fraction 200 may be removed within the aromatic recovery complex.

Further Processing

In one or more embodiments, the integrated process for conversion of a hydrocarbon stream comprising C5-C6 normal paraffins and iso-paraffins to enhanced value aromatics additionally includes subjecting the hydrocarbon stream 110 comprising C5-C6 normal paraffins and iso-paraffins to a desulfurization operation 50 prior to providing the generated desulfurized hydrocarbon stream 112 to the first reactor 10. For simplicity and to illustrate the various system arrangements, the desulfurization operation 50 is illustrated only on FIG. 3. However, it will be appreciated and is contemplated by the inventors that such desulfurization operation 50 may also be included with the system illustrated in FIGS. 1 and 2 as well as all other embodiments encompassed by the present disclosure. The desulfurization operation 50 may be any of a variety of desulfurization process known to those skilled in the art. In one or more embodiments, the desulfurization operation 50 may include hydrodesulfurization in a hydrotreater.

In one or more embodiments of the integrated process for conversion of a hydrocarbon stream comprising C5-C6 normal paraffins and iso-paraffins to enhanced value aromatics, the hydrocarbon stream 110 comprises less than 0.5 parts per million by weight (ppmw) of sulfur when provided to the first reactor 10. In various further embodiments, the hydrocarbon stream 110 comprises less than 0.3 ppmw of sulfur, less than 0.2 ppmw of sulfur, less than 0.1 ppmw of sulfur, or less than 0.05 ppmw of sulfur when provided to the first reactor 10. It will be appreciated that a hydrocarbon stream 110 which comprises a sulfur content greater than the prescribed quantity may be passed through the desulfurization operation 50 prior to providing the desulfurized hydrocarbon stream 112 in lieu of the hydrocarbon stream 110 to the first reactor 10. However, if the hydrocarbon stream 110 as provided comprises a sulfur content less than the prescribed quantity it may be passed directly to the first reactor 10 without processing in the desulfurization operation 50 or alternatively may still be subjected to processing in the desulfurization operation 50 to further reduce the sulfur content of the hydrocarbon stream 110.

EXAMPLES

The following examples illustrate features of the present disclosure but are not intended to limit the scope of the disclosure.

To verify the increase in conversion to value added aromatics products, specifically benzene and xylenes, with processes and systems in accordance with the present disclosure, laboratory scale demonstrations were completed for various processing schemes. Specifically, a light naphtha stream in accordance with the hydrocarbon steam 110 was processed. The composition of the light naphtha stream was in accordance with the composition of Table 1.

TABLE 1

Light Naphtha Feed Stream Composition (wt. %)

| Component | n-Paraffins | i-Paraffins | Naphthenes | Aromatics | Olefins | Total |
|---|---|---|---|---|---|---|
| C5 | 13.9 | 14.9 | 3.6 | | 0 | 32.4 |
| C6 | 14.9 | 27.8 | 4.5 | 3.3 | 0 | 50.4 |
| C7 | 0.0 | 16.8 | 0.1 | 0 | 0.2 | 17.1 |
| Total | 28.8 | 59.5 | 8.1 | 3.3 | 0.2 | |

Comparative Example 1

In Comparative Example 1, the light naphtha stream was processed using an aromatization reactor in accordance with the present disclosure to generate an aromatization product stream. To generate the aromatization product stream the light naphtha stream detailed in Table 1 was subjected to aromatization in the aromatization reactor at a temperature of 550° C. and a pressure of 0.98 bar (1 kg/cm² at a LHSV of 1 h$^{-1}$. Further, the catalyst provided in the aromatization reactor was a gallium modified H-MFI type zeolite comprising 2% by weight gallium. Further the H-MFI type zeolite comprised a silica to alumina ratio of 30. The composition of the resulting aromatization product stream is provided in Table 2. The presence of each component in the light naphtha stream is also provided for ease of reference.

The gallium modified H-MFI type zeolite catalyst was prepared in accordance with the following procedure. In a vessel mix 9.7 grams of HZSM-5 powder (such as CBV2314 (silica to alumina ratio of 23), or CBV3024 (SAR 30) purchased from Zeolyst) was combined with 50 ml of deionized-water at room temperature. Subsequently, 1.2 grams of gallium nitrate was dissolved in 10 ml of Distilled-water. Under continuous stirring at 250 rpm, the gallium nitrate solution was added dropwise to the HZSM-5 zeolite solution. The mixture was kept at room temperature under continuous stirring for 2 to 4 hours. Subsequently, the mixture solution was heated up to 85° C. to evaporate the moisture. The partially wet solid mixture was then transferred to a drying oven at 100° C. and kept in the oven overnight. Further, the dried solid was ground to powder form and calcined at 550° C. for 5 hours in a muffle furnace. The calcined powder product was then pelletized and crushed to 30-50 mesh catalyst granules for reactivity testing.

TABLE 2

Aromatization Product Stream Compositions (wt. %)

| Component | Light Naphtha Feed | Aromatization Product Stream |
|---|---|---|
| Fuel Gas | | 20.2 |
| Non-Aromatics | 100 | 0.0 |
| Benzene | | 32.4 |

TABLE 2-continued

Aromatization Product Stream Compositions (wt. %)

| Component | Light Naphtha Feed | Aromatization Product Stream |
|---|---|---|
| Toluene | | 32.6 |
| p-Xylene | | 12 |
| C9+ aromatics | | 2.8 |
| TOTAL | 100 | 100 |

Comparative Example 2

In Comparative Example 2, a reformate effluent fraction from a catalytic reforming unit in accordance with the present disclosure was provided to an aromatic recovery complex to process the various components of the reformate effluent fraction into product fractions. Specifically, the reformate effluent fraction without aromatized light naphtha was sent to an aromatic recovery complex, which included separation columns, benzene extraction, toluene transalkylation, xylene isomerization, and separation units to recover benzene, toluene and para-xylene. The produced toluene was sent to a transalkylation unit to produce xylenes. The transalkylation unit was operated with a catalyst of pt/pd on alumina, an operating temperature of 500° C., a LHSV of 1.5 h$^{-1}$, a H$_2$ to hydrocarbon molar ratio of 8, and an operating pressure of 50 psi. The composition of the reformate effluent fraction is provided in Table 3 and the composition of the products from the aromatic recovery complex are provided in Table 4. The breakdown in composition of the fuel gas is provided in Table 5.

TABLE 3

Reformate Effluent Fraction Compositions (wt. %)

| Component | Reformate Effluent Fraction |
|---|---|
| n-Paraffins | 4.5 |
| i-Paraffins | 11.5 |
| Naphthenes | 0.5 |
| Olefins | 1.2 |
| Aromatics | 82.3 |
| TOTAL | 100.00 |

TABLE 4

Aromatic Recovery Complex Products - Comparative Example 2 (wt. %)

| Component | Aromatic Recovery Complex Products - Comparative Example 2 |
|---|---|
| Fuel Gas | 2.02 |
| Non-Aromatics | 30.88 |
| Benzene | 7.23 |
| Toluene | 0.0 |
| p-Xylene | 27.65 |
| C9+ aromatics | 32.22 |
| TOTAL | 100 |

TABLE 5

Fuel Gas Composition (wt. %)

| Component | Fuel Gas |
|---|---|
| C1 | 30.3 |
| C2 alkanes | 20.5 |
| C2 alkenes | 4.7 |
| C3 and C4 | 44.5 |
| TOTAL | 100 |

Inventive Example 3

In Comparative Example 3, 10 metric tons (MT) of the aromatization product stream of Comparative Example 1 (Table 2) was combined with 100 MT of the reformate effluent fraction used in Comparative Example 2 (Table 3) for processing in the Aromatic Recovery Unit. The processing scheme was in accordance with FIG. 3 where toluene was sent to a transalkylation reactor from both the aromatic recovery complex and the separator. The composition of the products from the aromatic recovery complex are provided in Table 6.

TABLE 6

Aromatic Recovery Complex Products

| Component | Comparative Example 2 (MT/day) | Comparative Example 2 (wt. %) | Integrated Process Inventive Example 3 (MT/day) | Integrated Process Inventive Example 3 (wt. %) |
|---|---|---|---|---|
| Fuel Gas | 2.02 | 2.02 | 4.04 | 3.67 |
| Non-Aromatics | 30.88 | 30.88 | 30.88 | 28.07 |
| Benzene | 7.23 | 7.23 | 10.47 | 9.52 |
| Toluene | 0.0 | 0.0 | 0.0 | 0.0 |
| p-Xylene | 27.65 | 27.65 | 32.12 | 29.20 |
| C9+ aromatics | 32.22 | 32.22 | 32.50 | 29.55 |
| TOTAL | 100 | 100 | 110 | 100 |

It is noted that the integration of the aromatization product stream and the reformate effluent fraction results in an increase in aromatics overall as well as an increase in the desirable benzene and p-xylene specifically.

It should now be understood the various aspects of the integrated process and system for conversion of a hydrocarbon stream comprising C5-C6 normal paraffins and iso-paraffins to enhanced value aromatics are described and such aspects may be utilized in conjunction with various other aspects.

According to a first aspect, an integrated process for conversion of a hydrocarbon stream comprising C5-C6 normal paraffins and iso-paraffins to enhanced value aromatics, the process includes (i) providing the hydrocarbon stream comprising C5-C6 normal paraffins and iso-paraffins to a first reactor; (ii) passing the hydrocarbon stream through the first reactor, the first reactor being an aromatization reactor with an aromatization catalyst disposed therein to generate an aromatization product stream; (iii) passing the aromatization product stream from the first reactor through a separator, the separator configured to remove C1-C4 gases from the aromatization product stream to generate an aromatic rich stream; and (iv) passing the aromatic rich stream to an aromatic recovery complex to separate the aromatic rich stream into a benzene fraction, a toluene fraction, a para-xylene fraction, an aromatic bottoms fraction comprising C9+ aromatic hydrocarbons, and a non-aromatics fraction. Further, a reformate effluent fraction from a catalytic reforming unit is combined with the aromatization product stream prior to passing the aromatization product stream to the separator or is combined with the aromatic rich stream prior to passage to the aromatic recovery complex. Finally, the hydrocarbon stream comprises at least 60% by weight of normal paraffins and iso-paraffins having 5 or 6 carbon atoms.

A second aspect includes the process of the first aspect in which the process further comprises passing the toluene fraction from the aromatic recovery complex through a transalkylation reactor with a transalkylation catalyst disposed therein to generate a transalkylation effluent stream comprising xylene and benzene through a disproportionation reaction of toluene in the toluene fraction and passing the transalkylation effluent stream through the separator or directly to a component of the aromatic recovery complex.

A third aspect includes the process of the first or second aspect in which the separator additionally separates the aromatization product stream to generate a C5-C6 stream, a toluene stream, and a C8+ stream in lieu of the aromatic rich stream.

A fourth aspect includes the process of the third aspect in which the separator additionally separates the C5-C6 stream into a C5-C6 non-aromatic stream and a C5-C6 aromatic stream.

A fifth aspect includes the process of the second aspect in which in which the separator additionally separates the aromatic rich stream to generate a C5-C6 stream, a toluene stream, and a C8+ stream, wherein the toluene stream is passed to the transalkylation reactor, the C5-C6 stream is passed to the aromatic recovery complex, and the C8+ stream is passed to the aromatic recovery complex.

A sixth aspect includes the process of the third aspect in which the separator additionally separates the C5-C6 stream into a C5-C6 non-aromatic stream and a C5-C6 aromatic stream, wherein the C5-C6 non-aromatic stream is recycled back to the aromatization unit and the C5-C6 aromatic stream is passed to the aromatic recovery complex.

A seventh aspect includes the process of any of the second through sixth aspects in which the process further comprises splitting the aromatic bottoms fraction into a C9-C10 fraction and a C11+ fraction and providing the C9-C10 fraction to the transalkylation reactor along with the toluene fraction.

An eighth aspect includes the process of any of the first through seventh aspects in which the hydrocarbon stream comprises at least 75% by weight of normal paraffins and iso-paraffins having 5 or 6 carbon atoms.

A ninth aspect includes the process of any of the first through seventh aspects in which the hydrocarbon stream comprises at least 95% by weight of normal paraffins and iso-paraffins having 5 or 6 carbon atoms.

A tenth aspect includes the process of any of the first through seventh aspects in which the hydrocarbon stream consists essentially of normal paraffins and iso-paraffins having 5 or 6 carbon atoms.

An eleventh aspect includes the process of any of the first through tenth aspects in which the process further comprises subjecting the hydrocarbon stream to a desulfurization operation prior to providing the hydrocarbon comprising C5-C6 normal paraffins and iso-paraffins to the first reactor.

A twelfth aspect includes the process of any of the first through eleventh aspects in which the hydrocarbon stream comprises less than 0.5 parts per million of sulfur by weight when provided to the first reactor.

A thirteenth aspect includes the process of any of the first through twelfth aspects in which the aromatization catalysts comprises a gallium modified H-MFI type zeolite.

A fourteenth aspect includes the process of the thirteenth aspect in which the gallium modified H-MFI type zeolite comprises 1 to 3 weight percent gallium, or Zn, or La, or Co or Cr or Ce or Mo or Fe or Pt.

A fifteenth aspect includes the process of any of the first through fourteenth aspects in which the aromatization reactor is operated at a temperature of 500 to 600° C. and a pressure of 0.5 to 5 bar.

A sixteenth aspect includes the process of any of the first through fifteenth aspects in which the transalkylation catalysts comprises at least one catalyst selected from the group consisting of: Beta zeolite; IMF zeolite; ITH zeolite; MFI zeolite; MOR zeolite; MWW zeolite; NES zeolite; Rhenium metal; and a TUN zeolite.

A seventeenth aspect includes the process of any of the first through sixteenth aspects in which the transalkylation reactor is operated at a temperature of 400 to 450° C. and a pressure of 25 to 35 bar.

An eighteenth aspect includes the process of any of the first through seventeenth aspects in which the separator comprises one or more distillation units.

A nineteenth aspect includes the process of any of the first through eighteenth aspects in which the toluene fraction is substantially entirely converted to p-xylene.

A twentieth aspect includes the process of any of the first through nineteenth aspects in which the reformate effluent fraction from the catalytic reforming unit comprises at least 70 wt. % aromatics.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

For purposes of this disclosure, it is explicitly noted that indication that one stream or effluent is passed from one unit to another unit includes embodiments where the stream or effluent is passes directly from one unit to another unit as well as embodiments where there is an intervening system or unit which may substantially changes the composition of the stream or effluent between the units. As used in the present disclosure, passing a stream or effluent from one unit "directly" to another unit refers to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined.

As used in this disclosure, the term "effluent" refers to a stream that is passed out of a reactor, a reaction zone, or a separation unit following a particular reaction or separation. Generally, an effluent has a different composition than the stream that entered the separation unit, reactor, or reaction zone. It should be understood that when an effluent is passed to another system unit, only a portion of that system stream may be passed. For example, a slip stream may carry some of the effluent away, meaning that only a portion of the effluent may enter the downstream system unit. The term "reaction effluent" may more particularly be used to refer to a stream that is passed out of a reactor or reaction zone.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrocarbon stream" passing to a first system component or from a first system component to a second system component should be understood to equivalently disclose "hydrocarbon" passing to the first system component or passing from a first system component to a second system component.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned. For brevity, the same is not explicitly indicated subsequent to each disclosed range and the present general indication is provided.

As used in this disclosure and in the appended claims, the words "comprise," "has," and "include" and all grammatical variations thereof are each intended to have an open, non-limiting meaning that does not exclude additional elements or steps.

What is claimed is:

1. An integrated process for conversion of a hydrocarbon stream comprising C5-C6 normal paraffins and iso-paraffins to enhanced value aromatics, the process comprising:
   (i) providing the hydrocarbon stream comprising C5-C6 normal paraffins and iso-paraffins to a first reactor;
   (ii) passing the hydrocarbon stream through the first reactor, the first reactor being an aromatization reactor with an aromatization catalyst disposed therein to generate an aromatization product stream;
   (iii) passing the aromatization product stream from the first reactor through a separator, the separator configured to remove C1-C4 gases from the aromatization product stream to generate an aromatic rich stream; and
   (iv) passing the aromatic rich stream to an aromatic recovery complex to separate the aromatic rich stream into a benzene fraction, a toluene fraction, a para-xylene fraction, an aromatic bottoms fraction comprising C9+ aromatic hydrocarbons, and a non-aromatics fraction,
   wherein a reformate effluent fraction from a catalytic reforming unit is combined with the aromatization product stream prior to passing the aromatization product stream to the separator or is combined with the aromatic rich stream prior to passage to the aromatic recovery complex, and the hydrocarbon stream comprises at least 60% by weight of normal paraffins and iso-paraffins having 5 or 6 carbon atoms.

2. The process of claim 1 in which the process further comprises:
passing the toluene fraction from the aromatic recovery complex through a transalkylation reactor with a transalkylation catalyst disposed therein to generate a transalkylation effluent stream comprising xylene and benzene through a disproportionation reaction of toluene in the toluene fraction; and
passing the transalkylation effluent stream through the separator or directly to a component of the aromatic recovery complex.

3. The process of claim 2 in which the process further comprises:
splitting the aromatic bottoms fraction into a C9-C10 fraction and a C11+ fraction; and
providing the C9-C10 fraction to the transalkylation reactor along with the toluene fraction.

4. The process of claim 1 in which the separator additionally separates the aromatization product stream to generate a C5-C6 stream, a toluene stream, and a C8+ stream in lieu of the aromatic rich stream.

5. The process of claim 2 in which the separator additionally separates the aromatic rich stream to generate a C5-C6 stream, a toluene stream, and a C8+ stream,
wherein the toluene stream is passed to the transalkylation reactor, the C5-C6 stream is passed to the aromatic recovery complex, and the C8+ stream is passed to the aromatic recovery complex.

6. The process of claim 5 in which the separator additionally separates the C5-C6 stream into a C5-C6 non-aromatic stream and a C5-C6 aromatic stream, wherein the C5-C6 non-aromatic stream is passed to the aromatization reactor and the C5-C6 aromatic stream is passed to the aromatic recovery complex.

7. The process of claim 6 in which the process further comprises:
splitting the aromatic bottoms fraction into a C9-C10 fraction and a C11+ fraction; and
providing the C9-C10 fraction to the transalkylation reactor along with the toluene fraction.

8. The process of claim 1 in which the hydrocarbon stream comprises at least 75% by weight of normal paraffins and iso-paraffins having 5 or 6 carbon atoms.

9. The process of claim 1 in which the hydrocarbon stream comprises at least 95% by weight of normal paraffins and iso-paraffins having 5 or 6 carbon atoms.

10. The process of claim 1 in which the hydrocarbon stream consists essentially of normal paraffins and iso-paraffins having 5 or 6 carbon atoms.

11. The process of claim 1 in which the process further comprises subjecting the hydrocarbon stream to a desulfurization operation prior to providing the hydrocarbon comprising C5-C6 normal paraffins and iso-paraffins to the first reactor.

12. The process of claim 1 in which the hydrocarbon stream comprises less than 0.5 parts per million of sulfur by weight when provided to the first reactor.

13. The process of claim 1 in which the aromatization catalysts comprises a gallium modified H-MFI type zeolite.

14. The process of claim 10 in which the gallium modified H-MFI type zeolite comprises 1 to 3 weight percent gallium, or Zn, or La, or Co or Cr or Ce or Mo or Fe or Pt.

15. The process of claim 1 in which the aromatization reactor is operated at a temperature of 500 to 600° C. and a pressure of 0.5 to 5 bar.

16. The process of claim 1 in which the transalkylation catalysts comprises at least one catalyst selected from the group consisting of: Beta zeolite; IMF zeolite; ITH zeolite; MFI zeolite; MOR zeolite; MWW zeolite; NES zeolite; Rhenium metal; and a TUN zeolite.

17. The process of claim 1 in which the transalkylation reactor is operated at a temperature of 400 to 450° C. and a pressure of 25 to 35 bar.

18. The process of claim 1 in which the separator comprises one or more distillation units.

19. The process of claim 1 in which the toluene fraction is substantially entirely converted to p-xylene.

20. The process of claim 1 in which the reformate effluent fraction from the catalytic reforming unit comprises at least 70 wt. % aromatics.

* * * * *